United States Patent [19]

Jackson

[11] Patent Number: 4,495,045
[45] Date of Patent: Jan. 22, 1985

[54] ELECTROLYTIC DENTAL ETCHING APPARATUS

[76] Inventor: Thomas R. Jackson, 146 Renfro St., Mt. Airy, N.C. 27030

[21] Appl. No.: 589,155

[22] Filed: Mar. 13, 1984

[51] Int. Cl.³ .............................................. C25D 17/12
[52] U.S. Cl. ................................. 204/224 R; 204/271
[58] Field of Search ............ 204/129.6, 141.5, 129.46, 204/129.4, 224 R, 271

[56] References Cited

U.S. PATENT DOCUMENTS

| | | | |
|---|---|---|---|
| 2,590,927 | 4/1952 | Brandt | 204/224 R |
| 3,207,685 | 9/1965 | Pavlic | 204/224 R |
| 3,346,477 | 10/1967 | Wolfer | 204/129.46 |
| 3,704,220 | 11/1972 | Ashworth | 204/271 |

Primary Examiner—Thomas Tufariello
Attorney, Agent, or Firm—B. B. Olive

[57] ABSTRACT

An apparatus and method for electrolytic etching of cast dental alloys and pre-existing amalgam restorations provides a DC source for etching of the selected metalwork and an AC source for removal of the oxide coating produced by the etching process. Metal framework so etched and cleaned facilitate resin bonding as in resin-bonded retainers for fixed bridgework, resin-bonded crowns, resin-bonded orthodontic brackets, resin-coated amalgam and cast restorations, resin-coated partial denture clasps, and the like.

1 Claim, 2 Drawing Figures

ELECTROLYTIC DENTAL ETCHING APPARATUS

DESCRIPTION

1. Technical Field

The invention relates to dentistry and more specifically to apparatus and method for etching metal bridgework, orthodontic brackets amalgam restorations, and the like, preparatory to resin coating.

2. Background Art

A significant and relatively recent development in aesthetic operative dentistry has been the acid-etched composite resin bonding technique. The most recently developed composite resins used with this technique have high levels of micro-filled ceramic particles with excellent characteristics of color stability and wear resistance. The technique of etching the enamel with 30% to 50% phosphoric acid creates microscopic voids which the resin can invade instigating a micro-mechanical bond. This etching technique and subsequent micro-mechanical bond allows aesthetic materials to adhere to the enamel without the traditional deep preparations for retention. The etching technique is thus becoming increasingly popular.

Recently, fixed bridgework, periodontal splints and post-orthodontic splints have been bonded to enamel with acid etch resin techniques. Earlier techniques involved creating mechanical retention by machining a series of funnel-like preparations in the framework. The resin could then invade the preparations and lock the framework to the acid-etched enamel. There has also been introduced a technique for etching metal castings by corrosion. This process creates microscopic voids in the metal which can be invaded by resin for a micromechanical bond much like the phosphoric acid-etched resin bond of enamel. Electrolytically-etched frameworks for resin bonding of fixed bridge retainers has also been suggested. Lingual retainers have also been electrolytically etched in nitric acid and cleaned in hydrochloric acid with ultrasonic vibration. Another known procedure involves electrolysis of the casting in a dilute sulfuric acid solution.

The advantage of a microscopically-etched metal surface as well as an etched enamel surface is that the interdisposed bonding layer of resin is better protected without outside preparations. Also, the etched metal surface and enamel surface allow for a thinner and stronger resin layer. Most precious and non-precious metals can be etched by the electro-chemical process called electrostripping. Electrostripping is an electrochemical process similar to electroplating. Electrodeposition occurs at the cathode, or negative lead, whereas electrostripping occurs at the anode, or the positive lead. If an object is to be electrostripped, i.e., etched, it must, therefore, be attached to the anode in the electrolytic solution. When an object is electrostripped, the surface texture of the object after the metal is oxidized depends greatly on the crystalline grain structure of the alloy. Although most dental alloys can be electrolytically stripped, some alloys leave better etched textures than others due to the different phases in the alloys crystalline grain structure. After electrostripping is complete, the etched surface is usually cleaned in hydrochloric acid with ultrasonic vibration and is washed and then stored in alcohol to protect the etched surface prior to completion of bonding.

The quality and depth of the etch obtained by electrostripping depends on the applied amperage and voltage. Most etching rectifiers are designed to operate at about 0 to 25 volts DC and 0 to 1000 milliamps DC. The length of time of current exposure also determines the depth and quality of the etch. Thus, it is possible not only to underetch but also to overetch the casting. In order to obtain a uniform etch, it is necessary to maintain the current level substantially constant and preferably within ±5 to 10 milliamps of the proper current setting. The ammeter is monitored and operating conditions are adjusted as required.

Most electroplating units can be used to electrostrip an object. However, the half rectified wave form produced by conventional electroplating units while satisfactory for electroplating does not provide a uniform etch when the unit is used for electrostripping. A fully rectified and filtered wave form eliminates amperage fluctuation and provides a better unformity in electrolytic etching. Therefore, most electroplating units cannot be used for electrolytic etching of dental alloys. The most satisfactory electrolytic units incorporate a bridge diode and a filter circuit to provide a uniform amperage flow circuit.

The conventional etching technique also has the disadvantage of requiring the alloy to be etched in the laboratory and all surfaces not etched to be covered with a sticky wax and including the electrode. The process is time consuming and requires sticky wax removal and cleanup. Furthermore, if modifications are made during try-in, the bridge must be necessarily sent back to the laboratory for re-etching prior to bonding. Also, this technique does not allow etching of alloys already fixed in the oral cavity.

DISCLOSURE OF INVENTION

The apparatus and method of the present invention is designed to produce a cleaner and more uniform etch than is available with the previously-described conventional laboratory apparatus and methods. Of particular significance, the apparatus and method of the invention is adapted for use chairside without requiring that the metal be immersed in the laboratory beaker. The method of the invention is directed to etching an electrically conductive surface of a dental device preparatory to bonding a covering material to the surface which is etched. A DC voltage source is established with leads connected to the positive and negative terminals. The positive connected lead is attached to the electrically conductive dental device surface to be etched. The free end of the negative connected lead mounts means for retaining a dilute acid solution and etching is effected by intermittently touching portions of the surface being etched with the retainer means after which the etched surface is cleaned with an appropriate dilute acid. The etching and cleaning operation leaves an undesirable oxide coating. To remove such coating, the invention method also involves establishing a source of AC voltage and reconnecting the mentioned pair of leads to the AC source. The free end of one of the AC-connected leads is connected to the surface which has been etched. The free end of the other AC-connected lead mounts means for retaining a dilute acid and the etched surface is cleaned of oxide coating left over from the etching operation by intermittently touching the etched surface with the AC-connected lead having the dilute acid retainer means. The apparatus of the invention provides both the mentioned source of DC voltage as well as the mentioned source of AC voltage. The mentioned DCconnected and AC-connected leads may be one pair interchangeably connected to the DC and AC sources or separate pairs each connected to one of the sources. The method and apparatus of the invention thus allow the etching process to take place chairside without requiring the bridgework or other dental work being etched to be immersed in a laboratory beaker setup as in the prior art practice. Furthermore, the invention method and apparatus eliminate the need for coating the non-etched surfaces with sticky wax or the like.

BEST MODE FOR CARRYING OUT THE INVENTION

Figure 1:
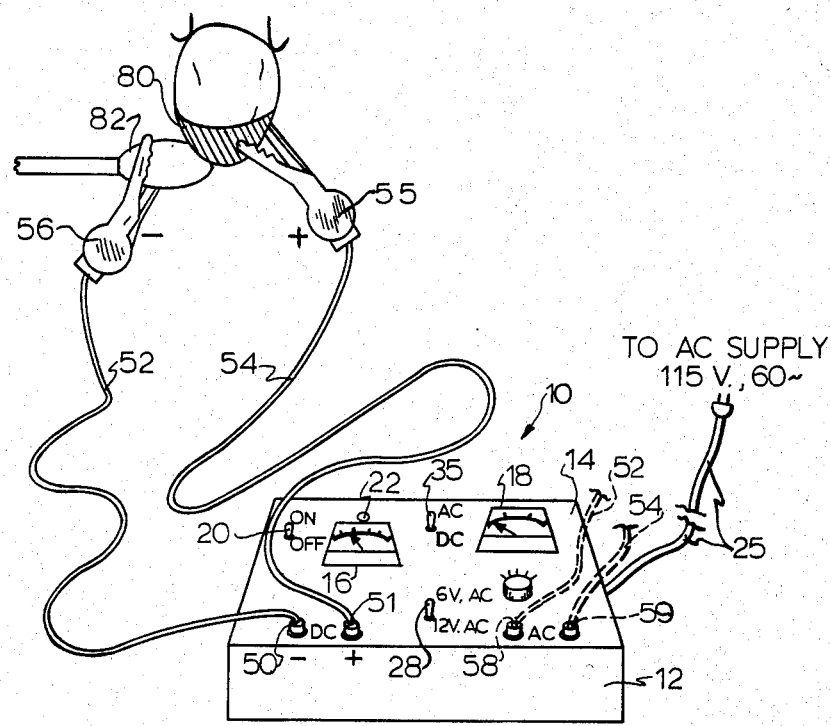
FIG. 1 is a schematic drawing of an apparatus adapted to provide both a DC source as well as an AC source for implementing the etching and cleaning techniques of the invention with the leads being shown in solid lines connected to the DC source and in dashed lines to the alternative AC source.

Making reference to the drawings, the apparatus 10 of the invention is housed in a cabinet 12 having a top panel 14. Panel 14 mounts a DC milliammeter 16 having a range of 0 to 1000 milliamps; a DC voltmeter 18 having a range of 0 to 15 volts; an on-off switch 20 in series with a red indicator light 22 to indicate when the source of AC power, normally 115 volts AC, supplied by power line 25 is connected; a single-pole, double-throw switch 28 enabling a selection of an output transformer voltage of either 6 volts AC or 12 volts AC from the step down transformer 30 (FIG. 2); a double-pole, double-throw switch 35; and a control knob 40 for setting a variable resistor 42 to control the DC output. Panel 14 also mounts a first pair of outlets 50 for receiving a suitable pair of leads 52, 54 having the respective positive clip connector 55 and negative clip connector 56 which are used in the manner later described.

Figure 2:
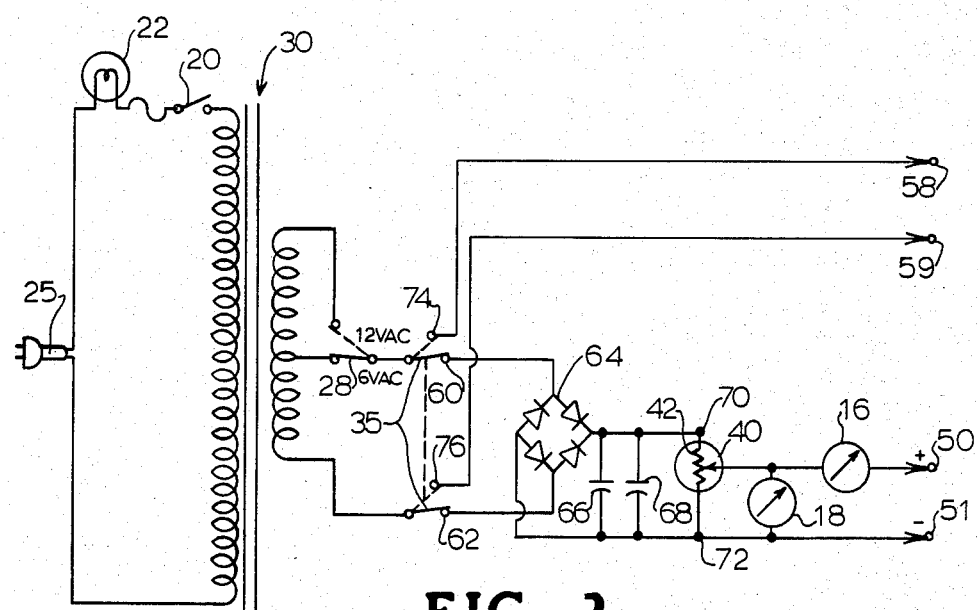
FIG. 2 is an electrical diagram of the circuit employed in the apparatus of FIG. 1.

Making reference to FIG. 2, it will be noted that when the power supply cord 25 is suitably connected to a source of AC voltage, typically 115 to 120 volts AC, 60 cycles, the red indicator light 22 is energized thus indicating to the operator that the apparatus is on. Switch 28 will normally be positioned initially in the 6 volt AC position and the double-pole, double-throw switch 35 will be positioned to apply the 6 volt AC voltage to terminals 60, 62 which applies the same voltage across the bridge network 64 which in conjunction with the filter capacitors 66, 68 produce a rectified, filtered DC voltage across terminals 70, 72 and across resistor 42. Thus, by adjustment of the control knob 40, a filtered and controlled, relatively-low DC voltage is made available at the outlet connectors 50, 51 with the current and voltage being measured by the respective milliammeter 16 and volt meter 18. When it is desired to increase the output DC voltage available at connectors 50, 51, switch 28 can be switched to the 12 volt AC position to produce a comparable increase in voltage at the connectors 50, 51.

With continuing reference to FIG. 2, it will also be noted that when the double-pole, double-throw switch 35 is moved to connect to terminals 74, 76 an AC voltage will be produced at connectors 58, 59 with the AC voltage in this mode of operation, at connectors 58, 59 being either 6 volts AC or 12 volts AC dependent on the position of switch 28. From this description it will be see that when the leads 52, 54 are connected to the connectors 50, 51, a DC voltage is available on connectors 55, 56 whereas when leads 52, 54 are connected to the respective connectors 58, 59, as indicated in dashed lines in FIG. 1, an AC voltage is available at the connectors 55, 56. Because of the brief exposure time and low AC voltage, the use of an AC ammeter and AC voltmeter has not been found necessary though may be employed. With this explanation, it is believed those skilled in the art will now fully appreciate the circuit aspects of the invention and the description next proceeds to operation of the invention apparatus.

As schematically illustrated in FIG. 1, the positive connection is directly to the metal framework, generally represented by the numeral 80, by means of the small clip 55. The negative or cathode clip 56 is attached to a cotton tip applicator 82 of the type used in dental offices. Prior to attaching the cathode clip 56 to the cotton tip applicator 82, the cotton end of the applicator 82 is dipped and saturated in dilute nitric acid or dilute sulfuric acid, depending on the alloy to be etched. Dilute nitric acid (5N) works well on alloys containing copper or silver phases whereas dilute sulfuric acid (10%) works best for alloys containing chromium and nickel phases. Non-precious metals, such as Rexillium III, which contain around 67% nickel and 30% chromium, etch best in dilute sulfuric acid. A few very inactive metals including platinum and gold are best etched by a mixture of concentrated nitric and hydrochloric acid, commonly known as Aqua Regia.

After the cotton tip of applicator 82 has been suitably saturated with the selected acid and clip 55 has been suitably secured to the metal framework 80, switch 20 is moved to the on position, switch 28 to the 6 volt AC position, switch 35 to the position for applying the 6 volt AC voltage to terminals 60, 62 and knob 40 is adjusted to provide 6 volts DC at connectors 50, 51. The cotton-tipped applicator 82 is then touched to the specific area of the metal framework 80 to be etched with the current being held within a range of 550-600 milliamps at 6 volts DC, with this operation taking place for approximately 2 minutes. This technique creates a miniature electrolytic bath at the cotton tip-metal framework interface. The direct current passes through the cathode into the cotton tip to the framework 80 and into the anode, i.e., clip 55, to complete the circuit. The described operation enabling the bridge or other metal framework to be spot etched takes place chairside and thus eliminates the previous practice of immersing the bridgework or other metal framework in a complicated laboratory setup and also eliminates the need for the non-etched surfaces to be coated with a sticky wax.

After the selected metal framework has been spot etched in all of the appropriate areas with direct current, the framework is washed with water and lightly dried and is then examined microscopically with loops for uniformity of the etch. If adequately etched, the dark oxide or slight metal membrane produced during the etching process is removed by changing the output applied to the respective clips 55, 56 from direct current to alternating current. Direct current tends to produce a deep, dark etch whereas alternating current on the other hand has been discovered to produce a white, superficial etch and has been found effective for cleaning the oxide off after the metal has been deep etched with direct current.

Once the etching process has been completed, switch 20 is opened, the leads 52, 54 are disconnected from the DC connector outlets 50, 51 and reconnected in the AC outlets 58, 59. Clip 55 is left attached to the metal framework 80. A clean cotton tip applicator 82 is employed and is dipped and saturated in 10% hydrochloric acid. Switch 28 is set at the 6 volt AC position, switch 35 is switched to apply the 6 volt AC voltage to terminals 74, 76 which allows the 6 volt AC voltage to be provided at the AC connector receptacles 58, 59. Clip 56 is attached to the new cotton tip applicator 82, switch 20 is moved to the on position and the cotton tip of the new applicator 82 is applied over the dark etched surfaces for approximately 30 to 60 seconds. This procedure has been found to be effective to remove all of the dark oxide metal residue and to leave a clean, bright, white etched surface. When this cleaning process utilizing alternating current has been completed, switch 20 is opened, clips 55, 56 are removed and the metal work 80 is washed in water and alcohol and then dried. The bridge, splint, or other device, forming the framework 80 is now ready for bonding to the enamel with conventional composite bonding techniques.

To increase retention of the dentin by short clinical crowns, the internal metal surfaces of the crown can be etched by placing the acid saturated cotton tip applicator inside the upside down crown with the anode clip, i.e, clip 55, being attached to the metal collar at the lingual of the crown. The spot etch technique just described can also be used to etch metal within the oral cavity for bonding to pre-existing amalgams, metal crowns or castings. Various applications include resin adhesion bonding of fixed bridgework to metal restorations, orthodontic bonding of brackets or splints to pr-existing metal restorations, repair of ceramic or acrylic bridgework in the mouth by acrylic coating of exposed metal, coating of pre-existing amalgam or cast restorations in the mouth for aesthetic reasons and resin coating of partial denture clasps for aesthetic reasons.

To electrolytically etch amalgam or cast restorations in the mouth, special care must be taken. Although the applied voltage is low, i.e., six volts DC, if both electrodes are carelessly touched to wet soft tissue, a very slight electric shock may be felt. While the voltage is not high enough to cause any damage, it can be about as uncomfortable as an electric pulp tester set on medium strength. Of course, if the clips are applied as diagrammed in FIG. 1, the patient will feel no current since there will be no circuit traveling through the soft tissues. It is also desirable that the area being etched be carefully isolated with a rubber dam to keep the dilute acid off the surrounding tissues with an immediately water wash being desirable in the event of unexpected contact between the dilute acid and any surrounding tissue. Care must also be taken when etching in the mouth not to overheat the restoration and thereby thermally damage the pulp. Therefore, it is desirable to use a thermal probe with a digital-type thermal probe being desirable for this application. In general, the temperature should never exceed 140° F. and if excess temperature is sensed, the circuit may be momentarily broken by simply removing the anode clip 55 to allow time for the heat to dissipate. Different alloys will be noted as having different heating characteristics due to the difference in their internal resistance to electric current.

What is claimed is:

1. A chairside apparatus for etching and thereafter removing any oxide coating from an electrically conductive surface of an installed dental device in a patient preparatory to bonding a covering material to the surface so etched, comprising:
   (a) AC-energized power supply means providing:
      (i) a source of DC voltage within the range of 6–12 volts;
      (ii) a source of AC voltage within the range of 6–12 volts;
   (b) a pair of leads;
   (c) means enabling one end of said pair of leads to be selectively connected to either said DC or AC source to provide the corresponding selected said voltage at the opposite terminal ends thereof;
   (d) a disposable fibrous swab mouunted on the terminal end of the first of said leads and being sufficiently small in size to enable the said etching and oxide coating removal to be accomplished chairside with said device installed;
   (e) a dilute acid stored in said swab; and
   (f) means for detachably connecting the terminal end of the second of said leads to a selected location on said electrically-conductive surface such that said etching may be accomplished by intermittently touching said swab to said surface when said leads are connected to said DC source and removal of said coating can be accomplished by intermittently touching said swab to said surface when said leads are connected to said AC source.

* * * * *